United States Patent [19]

Shiraki et al.

[11] Patent Number: 4,827,025

[45] Date of Patent: May 2, 1989

[54] PROCESS FOR THE PRODUCTION OF AROMATIC CARBOXYLIC ACIDS

[75] Inventors: Shigemi Shiraki; Kenichi Mizuno, Both of Iwakuni, Japan

[73] Assignee: Mitsui Petrochemical Industries, Ltd., Tokyo, Japan

[21] Appl. No.: 97,800

[22] Filed: Sep. 16, 1987

[30] Foreign Application Priority Data

Sep. 26, 1986 [JP] Japan .................................. 61-226131

[51] Int. Cl.$^4$ .......................................... C07C 51/265
[52] U.S. Cl. ...................................... 562/414; 562/416
[58] Field of Search ................................. 562/414, 416

[56] References Cited

U.S. PATENT DOCUMENTS

| | | | |
|---|---|---|---|
| 3,086,993 | 4/1963 | Bulkley | 562/414 |
| 4,357,475 | 11/1982 | Hanutier | 562/414 |
| 4,593,122 | 6/1986 | Hashizume | 562/414 |

*Primary Examiner*—Michael L. Shippen
*Attorney, Agent, or Firm*—Flynn, Thiel, Boutell & Tanis

[57] ABSTRACT

A process for the production of aromatic carboxylic acid in a continuous manner by oxidizing an alkyl aromatic compound in the liquid phase with an oxygen-containing gas in the presence of heavy metal compound(s) and/or bromine-containing compound, which process is characterized by that a part of the reaction gas delivered from the reactor and freed from the condensing components is recirculated by returning it to the reactor at a portion within the gas region. Said process permits to produce aromatic carboxylic acids of high quality, while eliminating the troubles due to foaming occurring on the liquid surface in the reactor.

8 Claims, 1 Drawing Sheet

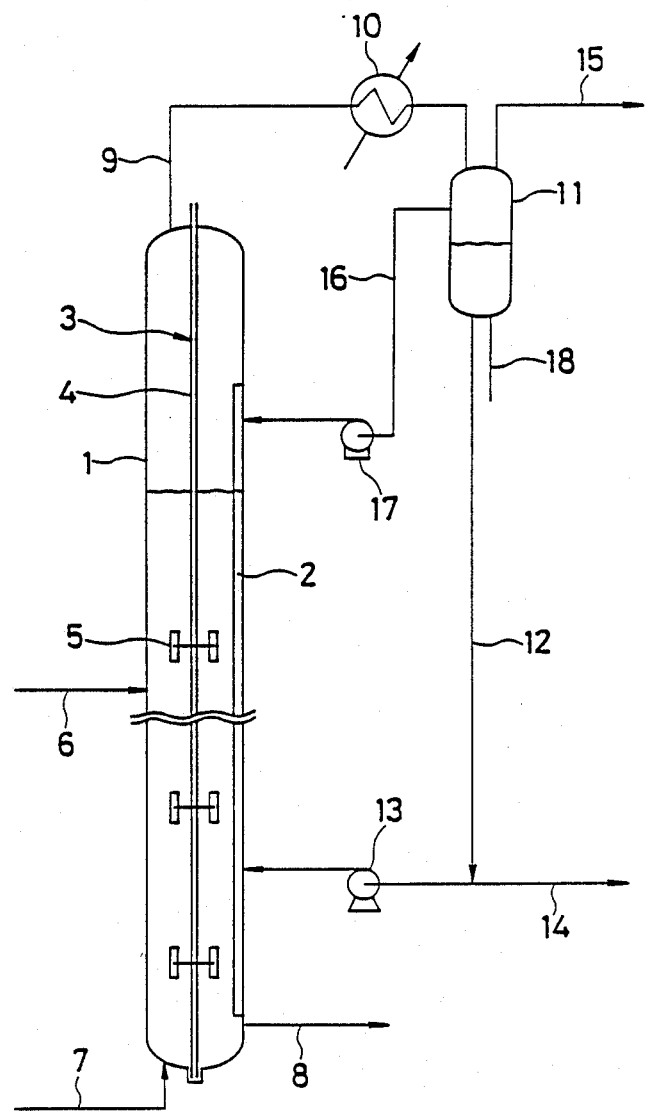

PROCESS FOR THE PRODUCTION OF AROMATIC CARBOXYLIC ACIDS

BACKGROUND OF THE INVENTION

1. Field of the Invention

The present invention relates to a process for the production of aromatic carboxylic acids, in particular, to a process which permits to produce aromatic carboxylic acids of high quality by a catalyzed liquid/gas oxidation of alkyl aromatics, while eliminating the troubles due to foaming occurring on the liquid surface in the reactor.

2. Description of the Prior Art

There have been proposed processes for the production of aromatic carboxylic acids by oxidizing alkyl aromatic compounds, such as, paraxylene etc., in liquid phase by oxygen-containing gas in the presence of an oxidation catalyst, in which (1) the solvent vapor evaporated in the reactor is separated from the exhausted reaction gas by condensing it and the thus condensed solvent is recirculated by returning it to the reactor at its bottom (Japanese Patent Application Lay-Open No. 112044/1986 and the corresponding foreign Applications, namely, U.S. Pat. No. 4,593,122 and European Patent Application Lay-Open No. 125,341A) and in which (2) a predetermined proportion of the reaction gas delivered from the reactor is recirculated by turning it back into the reactor at a portion within the region of liquid phase (Japanese Patent Application Lay-Open No. 36439/1985 and the corresponding foreign Applications, namely, Belgian Pat. No. 90342, Brazilian Patent Application Lay-Open No. 8505367 and Spanish Pat. No. 8609191).

It had thus been recognized that lower reaction temperature and lower reaction pressure can be employed and a product of terephthalic acid (TPA) exhibiting higher light transmittance can be produced by recirculating the solvent or the reaction gas by turning them back to the reactor, in the manner explained above. Especially, in the above case (2), the oxidation reaction is effected with increasing oxygen partial pressure in the gas phase of the reaction system, whereby a reaction mixture containing a product of TPA having better light transmittance is obtained. It was reported that the hue of the polyester obtained was superior even though the content of 4-carboxy benzaldehyde (abbreviated hereinafter as 4-CBA) amounted to more than 500 ppm, when the product was subjected to an after-oxidation treatment, and that an ultrapure product having a light transmittance ($T_{340}$) of some 95% could be obtained, when the reaction was carried out in such a condition that the content of 4-CBA amounted to 200-300 ppm.

In the above mentioned process (2), in which a predetermined proportion of the reaction gas delivered from the reactor is recirculated by turning it back to the reactor continuously at a portion within the liquid layer, although the advantageous effect suggested above can be attained, a considerable foaming on the liquid surface occurs. In a continuous production of an aromatic carboxylic acid by oxidizing an alkyl aromatic with oxygen-containing gas in liquid phase in the presence of a heavy metal compound and/or bromine-containing compound, the oxygencontaining gas is fed usually to the reactor at a portion within the region of liquid layer and the reaction is conducted under agitation, so that foaming occurs on the surface of liquid layer. The mist of reaction liqor containing the aromatic carboxylic acid suspended or dissolved therein, originated from collapsed foam will be entrained in the rising vapor and is carried over to the installation units, such as, heat exchanger, distillation tower and so on, in the succeeding process line, bringing about thereby problems, such as clogging of the line by the deposited carboxylic acid etc.

In the above prior process (2), the reaction gas after passing through the liquid layer in the reactor is recirculated by being returned to a portion in the region of liquid layer, so that such foaming problem is still more facilitated.

With the growing trend in recent years to the employment of large size units, the lifting velocitiy of the vapor in the gas layer at upper portion of the reactor becomes higher, so that troublesome problems caused by the foaming as mentioned above have grown to a matter of still greater significance. Therefore, it had become an inevitable technical requirement to solve the foaming problem for employing large size units.

Another important problem for effecting recirculation of a part of the reaction gas freed from the condensing components by returning it to a portion of the region of liquid phase in the reactor is a large power consumption by the gas recirculation blower. This constitutes also a substantial shortcoming in this process, since the gas compression energy required for overcoming the hydrostatic head by the liquid layer depth which has now become greater due to the employment of large size unit is considerably large.

SUMMARY OF THE INVENTION

An object of the invention is to provide a process for producing aromatic carboxylic acids, in which the problems in the techniques of the prior art are eliminated and further advantages are realized.

Another object of the present invention is to provide a process for the production of aromatic carboxylic acids, in which the above mentioned foaming problems are excluded and the energy consumption is made lower.

A further object of the present invention is to provide a process which permits production of high quality aromatic carboxylic acids by employing higher oxygen partial pressure in the gas phase of the reactor.

A still further object of the present invention is to provide a process for the production of aromatic carboxylic acid, in which the loss of the solvent by combustion during the oxidation reaction can relatively be reduced.

Thus, the present invention relates to a continuous process for the production of aromatic carboxylic acid by oxidizing an alkyl aromatic compound in liquid phase with an oxygen-containing gas in the presence of heavy metal compound and/or bromine-containing compound, characterized by that a part of the reaction gas delivered from the reactor and freed from the condensing components is recirculated by turning it back to the reactor at a portion in the gas layer.

BRIEF DESCRIPTION OF THE DRAWING

The single Drawing appended shows an explanatory flow sheet of an embodiment of the apparatus for carrying out the process according to the present invention.

DETAILED DESCRIPTION OF THE INVENTION

[As to the alkyl aromatic compound and the aromatic carboxylic acids]

The alkyl aromatic compounds to be used in the process according to the present invention include, for example, toluene, o-, m- and p-xylene, trimethylbenzene, methylnaphthalene, dimethyllnaphtbulene and so on, beside other compounds, such as, p-tolualdehyde, p-toluic acid etc.

The aromatic carboxylic acids obtained from the above compounds include, for example, benzoic acid, o-phthalic acid, isophthalic acid, terephthalic acid, benzenetricarboxylic acid, naphthoic acid, naphthalenedicarboxylic acid and so on.

In a preferred embodiment of the invention, p-xylene is oxidized into terephthalic acid.

[As to the solvent]

Since the present invention deals with a liquid phase oxidation, the oxidation is carried out in a solvent. As to the reaction solvent, there may be enumerated, for example, fatty acids, such as, acetic acid, propionic acid, n-butyric acid, isobutyric acid, n-valerianic acid, trimethyl acetic acid, caproic acid and so on and mixtures of these with water. Among these, acetic acid and mixture thereof with water are preferred, as will be explained later on.

[As to the catalyst]

The catalyst to be employed in the process according to the present invention consists of heavy metal compound(s) and/or a bromine-containing compound.

As to the heavy metal compound, there may be exemplified compounds of nickel, cobalt, iron, chromium, manganese etc. Concrete examples of these compounds include cobalt acetate, cobalt naphthenate, cobalt bromide, manganese acetate, manganese naphthenate, manganese bromide, nickel acetate, nickel bromide, iron acetate, iron bromide, chromium acetate, chromium bromide and so on. The bromine-containing compounds include, beside those which are included in the above explained heavy metal compounds, hydrogen bromide and tetrabromoethane as well as lower aliphatic carboxylic acid bromoalkanol esters having 4–6 carbon atoms, such as, dibromo-ethyl acetate, monobromopropyl acetate and so on.

In a preferred embodiment, a cobalt compound and a manganese compound are employed concurrently with a bromine-containing compound.

The amount of cobalt compound is usually within a range from 10 to 10,000 ppm, preferably from 100 to 3,000 ppm, based on the weight of the solvent. The manganese compound is used in general at an atomic ratio relative to cobalt in a range from 0.001 to 2. The bromine-containing compound is used usually at an atomic ratio to cobalt in a range from 0.1 to 5.

[As to the oxygen-containing gas]

The oxygen-containing gas to be employed in the process according to the present invention is usually a gas mixture of oxygen diluted by an inert gas, such as, air or oxygen-enriched air.

[As to other reaction conditions]

The temperature of the oxidation reaction in the process according to the present invention is usually between 150° C. and 270° C., preferably between 170° and 220° C. The reaction pressure should be higher than that necessary to maintain the liquid phase of the reaction mixture at the reaction temperature and may, in general, be in the range from 5 to 40 $Kg/cm^2$ gauge. The reaction duration may be such that the residence time in the reactor will be in a range from 20 to 180 minutes, though it may depend on the each specific size and the capacity of the reactor. The concentration of water in the reaction system may, in general, be in the range from 3 to 30% by weight, preferably from 5 to 15% by weight. The adjustment of the water content in the reaction system can be attained by exhausting a suitable proportion of the condensate separated from the delivered reaction gas, that contains the condensed water, out of the reaction system by branching it from the portion of the condensate to be recirculated, as will be explained later on.

Below, the invention will further be described with reference to the Drawing appended.

As shown in the Drawing, the reactor 1 is equipped with a baffle plate 2 near the inner surface of the reactor shell and with a stirrer 3 at its center which is composed of a shaft 4 and a plurality of stir vanes 5. While the reactor 1 is usually of an agitation type, as shown in FIG. 1, the stirrer 3 may, on occasion, be dispensed with. The alkyl aromatic compound and the solvent are fed to the reactor 1 from a raw material feed line 6 and the oxygen-containing gas is supplied thereto via a gas feed line 7. The reaction product is discharged from the reaction system via a product discharge line 8. At the top of the reactor 1, a reaction gas delivery line 9 is arranged, in which a heat exchanger 10 for separating the condensing components from the delivered reaction gas is disposed. It is possible to install a distillation tower (not shown) instead of or together with the heat exchanger 10. The condensing components condensed upon cooling by the heat exchanger 10 are separated from the gas components and are collected in a separator drum 11 as condensate. The separator 11 is provided with a gas recirculation line 16, a gas exhaustion line 15, a condensate outlet line 12 and a sampling line 18. A part of the condensate is recirculated within the system by returning it continuously to the reactor 1 by a pump 13 and the other part thereof may, if necessary, be discharged out of the system. Here, it is possible to recirculate all or a part of the condensate within the system by returning it to the region of the gas phase, instead of returning to the region of liquid layer of the reactor. The gas separated from the condensing components is partly exhausted out of the system from an exhaustion line 15 and partly turned back to the gas layer of the reactor via a gas circulation line 16 by a blower 17. Here, the gas to be returned to the gas region of the reactor 1 is, on requirement, cooled by a cooler (not shown) to a temperature of, for example, 150° C. or lower, preferably to a temperature of 120° C. or lower. Thus, by returning the separated and cooled reaction gas to the gas layer of the reactor, the effect for suppressing the foaming occurring on the surface of liquid layer of the reactor will still more be emphasized. The proportion of the reaction gas recirculated to the reactor 1 relative to the gas exhausted out of the reaction system (entire exhaustion gas) may usually be in the range from 5 to 400%, preferably from 10 to 200%, depending on each particular reactor and other conditions employed. The foam suppressing effect has been approved within the above range and, therefore, the actual proportion should be settled at a value in this range at which the entrainment of mist of liquid reaction mixture will not be facilitated by the recirculating gas itself. The portion at which the delivered reaction gas to be recirculated is returned to the reactor 1 may be everywhere the substantial foam suppression effect is able to be attained, while a portion in the reactor at a level higher than one tenth of the reactor diameter above the liquid surface may be preferred.

It is possible to bring about a swirling current in the gas region above the liquid surface of the reactor by arranging the nozzle for introducing the recirculation gas into the reactor so as to discharge the gas in an eccentric direction in order to contribute to collapsing of foams appearing on the liquid surface efficiently and, at the same time, to blow the liquid droplets or mist floating in the gas space onto the reactor shell wall to collect them, in a manner similar to a cyclone separator. The direction of arrangement of the nozzle may be such that a substantial swirling stream will be formed and it can be, for example, at an angle of from 0° to 80° to the tangent.

The aromatic carboxylic acid formed by the process according to the present invention may be put into commercial product by subjecting the reaction mixture to a usual treatment process, such as, crystallization or so on or, for specific uses, to known treatment procedures including crystallization, lower temperature afer-oxidation, higher temperature after-oxidation, hydrogenation purification and so on.

By the process according to the present invention, it is possible to increase the oxygen partial pressure in the gas phase due to the employment of recirculation of a part of the reaction gas, which results in an increase in the reaction pressure as compared with the case without recirculation of the reaction gas. Therefore, aromatic carboxylic acids, such as, terephthalic acid and so on, exhibiting superior light transmittance (will be explained afterward), as in the case of the Japanese Patent Application Lay-Open No. 36439/1985 previously mentioned, can be obtained with the further advantage of exclusion of the foaming problem encountered in the prior art processes.

Another advantage of the present invention consists in the relative decrease in the combustion loss of the solvent, such as acetic acid, during the oxidation reaction. This is achieved by the fact that the reaction condition can be relieved in the process according to the present invention for attaining a comparable degree of oxidation, as contrasted to the process without employing the gas recirculation, since the oxygen partial pressure in the gas phase can be elevated. Here, it is able to realize such advantageous effects with lower gas recirculation power consumption by the reduction of compression pressure due to exclusion of hydrostatic head. This is an important advantage as contrasted to the previously mentioned process of the Japanese Patent Application Lay-Open No. 36439/1985.

PREFERRED EMBODIMENT OF THE INVENTION

In the following, the invention will be explained concretely by way of Example.

In the Example, the content of 4-carboxybenzaldehyde (4-CBA) in the product of terephthalic acid was determined by polarography and the light transmittance o the terephthalic acid product was represented by light transmittance $T_{340}$ (%) at 340 mμ of a 2 N potassium hydroxide aqueous solution containing terephthalic acid at a concentration of 15% by weight.

EXAMPLE 1

An oxidation reactor as shown in FIG. 1 was employed. The reactor 1 was provided with a stirrer 3 composed of a rotary shaft 4 supported at two intermediate portions and at the bottom (not shown) and of stir vanes 5 disposed in five stages. The reactor 1 consists of a vertical cylinder made of titanium having an inner diameter of 400 mm and a length (height) of 7 m, which is provided with a gas feed line 7 for supplying an oxygen-containing gas, a raw material feed line 6 for feeding the raw material of paraxylene and a product discharge line 8 for discharging the liquid reaction mixture. The reactor was charged initially with 310 kg of acetic acid, 22 kg of water, 1637 g of cobalt acetate, 8.1 g of manganese acetate and 880 g of tetrabromoethane and the mixture was maintained at a temperature of 186° C. and a pressure of 12.8 Kg/cm² gauge. The oxidation reaction was conducted continuously while feeding 110 kg/hr of p-xylene, 460 kg/hr of acetic acid, 30 kg/hr of water, 2460 g/hr of cobalt acetate, 12.2 g/hr of manganese acetate and 1320 g/hr of tetrabromoethane via the raw material feed line 6 and while feeding air from the gas feed line 7 at such a rate that the oxygen concentration in the delivered reaction gas would have reached to 6.4% by volume. The delivered reaction gas freed from the condensing components in the separator drum 11 in an amount that corresponds to 30% by volume of the exhaustion gas exhausted via the gas exhaustion line 15 was recirculated through the return line 16 by the blower 17 during the operation. The injection nozzle for the recirculation gas was located in the gas region of the reactor 1 at a site of 600 mm height above the liquid level and the gas introduced was directed at an angle of 30° to the tangent of the reactor shell towards the direction of rotation of the stirrer 3. The liquid reaction mixture was discharged out of the reactor at the discharge line 8 in such a rate that the residence time of the liquid reaction mixture within the reactor would have amounted to 40 minutes. The liquid reaction mixture thus discharged was subjected to solid/liquid separation and the product was washed sufficiently with acetic acid. The terephthalic acid product obtained exhibited a light transmittance $T_{340}$ of 73.7% and a 4-CBA content of 605 ppm. The power consumption by the gas circulation blower was as high as 3 KW.

In this condition, the test run was able to continue for one week without interruption. A sample of liquid reaction mixture taken from the sampling line 18 was almost transparent, though a scarce turbidity was observed. After the uninterrupted successive test run had been terminated, the internal condition of the heat exchanger 10 was inspected by opening it, with the result being that almost no deterioration of the internal surfaces was detected.

COMPARISON EXAMPLE 1

The procedures of Example 1 were repeated with the only exception being that the reaction gas was returned to the reactor 1 through the line 16 at a position of 500 mm height from the bottom of the reactor within the liquid layer. After 8 hours from the commencement of the continuous operation, the test run was stopped due to the fact that the pressure drop between the inlet and the outlet of the heat exchanger 10 had reached to an intolerable value. By inspecting the inside of the heat exchanger 10 by opening it, deposition of crystalline terephthalic acid was found on the inlet side and the pass through opening rate in the cooling pipe row of the heat exchanger had been reduced to about 20%. The product thus obtained exhibited a light transmittance of 70.5% and a 4-CBA content of 666 ppm, which were at the level nearly the same with that of Example 1, while the power consumption by the gas circulation blower was raised to 7 KW, which at the end of the test run had reached to about 9 KW.

What is claimed is:

1. In a continuous process for producing an aromatic carboxylic acid in a cylindrical reaction vessel containing a lower liquid phase and an upper gas phase, comprising continuously oxidizing an alkyl aromatic compound in said liquid phase with an oxygen-containing gas in the presence of a catalyst containing a heavy metal compound, a bromine-containing compound or both of said heavy metal compound and said bromine-containing compound, continuously withdrawing a gaseous effluent containing a condensable vapor and noncondensable gas from the gas phase of said reaction vessel, continuously condensing said condensable vapor to obtain a condensate and continuously separating said condensate from said noncondensable gas, the improvement for minimizing the amount of said liquid phase that is entrained in said gaseous effluent, which comprises: continuously dividing the entirety of said noncondensable gas into an exhaust gas portion and a recirculation gas portion so that the amount of said recirculation gas portion is from 5 to 400% by volume, based on the amount of said exhaust gas portion; continuously discharging said exhaust gas portion from the reaction system; continuously flowing a stream consisting of the entirety of said recirculation gas portion into said gas phase of said reaction vessel at a location which is spaced above the upper surface of said liquid phase at least a distance equal to 0.1 times the diameter of said reaction vessel, said stream being directed into said gas phase at an angle of from 0 to 80° relative to a tangent to the wall of said reaction vessel whereby said stream swirls in said gas phase, causes collapse of foam on the upper surface of said liquid phase, blows liquid droplets and mist that are floating in said gas phase against the wall of said reaction vessel so that they collect on said wall and increases the partial pressure of oxygen in said gas phase.

2. A process as claimed in claim 1 in which the reaction temperature in said liquid phase is from 170° to 220° C. and including the step of cooling said recirculation gas portion to a temperature of 120° C. or lower before flowing it into said gas phase in said reaction vessel.

3. A process for continuously producing an aromatic carboxylic acid, which comprises: in a reactor, oxidizing an alkyl aromatic compound in a liquid phase with an oxygen-containing gas in the presence of at least one heavy metal compound and/or bromine-containing compound, continuously withdrawing a gaseous effluent from said reactor, condensing the condensable component of said effluent and removing the condensate from the noncondensed gas, separating said noncondensed gas into an exhaust portion and a recirculation portion wherein the amount of said recirculation portion is from 5 to 400% by volume, relative to said exhaust portion, discharging said exhaust portion from the reaction system, continuously flowing said recirculation portion into the gas phase in said reactor so as to increase the partial pressure of oxygen in said reactor and, at the same time, to form a centrifugal swirling gas flow within said gas phase.

4. A process according to claim 3, wherein a part of said condensate is recirculated by returning it to the liquid phase in the reactor.

5. A process according to claim 3, wherein the alkyl aromatic compound is selected from the group consisting of toluene, o-, m- and p-xylene, trimethylbenzene, methylnaphthalene, dimethylnaphthalene, p-tolualdehyde and p-toluic acid.

6. A process according to claim 4, wherein the alkyl aromatic compound is selected from the group consisting of toluene, o-, m- and p-xylene, trimethylbenzene, methylnaphthalene, dimethylnaphthalene, p-tolualdehyde and p-toluic acid.

7. A process according to claim 3, wherein the aromatic carboxylic acid is selected from the group consisting of benzoic acid, o-phthalic acid, isophthalic acid, terephthalic acid, benzene-tricarboxylic acid, naphthoic acid and naphthalenedicarboxylic acid.

8. In a continuous process for producing terephthalic acid in a cylindrical reaction vessel containing a lower liquid phase and an upper gas phase, comprising continuously oxidizing paraxylene in said liquid phase in which said para-xylene is dissolved in a solvent of acetic acid and water, with an oxygen-containing gas in the presence of a catalyst containing a heavy metal compound, a bromine-containing compound or both of said heavy metal compound and said bromine-containing compound and at a temperature of from 170° to 220° C. and a pressure of from 5 to 40 kg/cm$^2$ (gauge), continuously withdrawing a gaseous effluent containing a condensable vapor and noncondensable gas from the gas phase of said reaction vessel, continuously condensing said condensable vapor to obtain a condensate and continuously separating said condensate from said noncondensable gas, the improvement for minimizing the amount of said liquid phase that is entrained in said gaseous effluent, which comprises: continuously dividing the entirety of said noncondensable gas into an exhaust gas portion and a recirculation gas portion so that the amount of said recirculation gas portion is from 10 to 200% by volume, based on the amount of said exhaust gas portion; continuously discharging said exhaust gas portion from the reaction system; continuously cooling said recirculation gas portion to a temperature of below 120° C. and then flowing a stream consisting of the entirety of said recirculation gas portion into said gas phase of said reaction vessel at a location which is spaced above the upper surface of said liquid phase a distance equal to or larger than 0.1 times the diameter of said reaction vessel, said stream being directed into said gas phase at an angle of from 0 to 80° relative to a tangent to the wall of said reaction vessel whereby said stream swirls in said gas phase, causes collapse of foam on the upper surface of said liquid phase, blows liquid droplets and mist that are floating in said gas phase against the wall of said reaction vessel so that they collect on said wall, and increases the partial pressure of oxygen in said gas phase.

* * * * *